(12) United States Patent
Lipman et al.

(10) Patent No.: US 7,105,027 B2
(45) Date of Patent: Sep. 12, 2006

(54) SELF-ALIGNING KNEE PROSTHESIS

(75) Inventors: Joseph D. Lipman, New York, NY (US); Russell F. Warren, Greenwich, CT (US); Thomas L. Wickiewicz, Franklin Lakes, NJ (US); Timothy M. Wright, Stamford, CT (US); Donald L. Bartel, Ithaca, NY (US); Frank Hoffman, Prutting (DE); Christoph Fankhauser, Solothurn (CH); Daniel Delfosse, Bern (CH); Walter Supper, Bettlach (CH)

(73) Assignee: Mathys Medical Ltd., Bettlach (CH)

( * ) Notice: Subject to any disclaimer, the term of this patent is extended or adjusted under 35 U.S.C. 154(b) by 130 days.

(21) Appl. No.: 10/356,657

(22) Filed: Jan. 31, 2003

(65) Prior Publication Data

US 2004/0006394 A1 Jan. 8, 2004

(51) Int. Cl.
*A61F 2/38* (2006.01)

(52) U.S. Cl. .................................... 623/20.29
(58) Field of Classification Search .............. 623/20.28, 623/20.29, 20.21, 20.3, 20.33, 20.23
See application file for complete search history.

(56) References Cited

U.S. PATENT DOCUMENTS

| | | | |
|---|---|---|---|
| 4,224,696 A | | 9/1980 | Murray et al. |
| 4,340,978 A | | 7/1982 | Buechel et al. |
| 4,586,933 A | * | 5/1986 | Shoji et al. ............... 623/20.29 |
| 5,064,437 A | * | 11/1991 | Stock et al. ............. 623/20.29 |
| 5,314,482 A | | 5/1994 | Goodfellow et al. |
| 5,824,100 A | | 10/1998 | Kester et al. |
| 5,871,542 A | * | 2/1999 | Goodfellow et al. ...... 623/20.16 |
| 5,964,808 A | * | 10/1999 | Blaha et al. ............. 623/20.28 |

FOREIGN PATENT DOCUMENTS

| | | |
|---|---|---|
| DE | 195 29 824 A1 | 2/1997 |
| EP | 0 442 330 A2 | 8/1991 |
| EP | 0 734 700 A2 | 10/1996 |
| EP | 0 734 701 A2 | 10/1996 |
| FR | 676916 | 2/1930 |
| JP | 4-218155 | 8/1992 |

* cited by examiner

*Primary Examiner*—Pedro Philogene (57) ABSTRACT

A prosthesis for repairing a knee is made with an insert sandwiched between a femoral component and a tibial tray. The parts are shaped so that both the femoral component and the tibial tray will slidingly interface with the insert during motion of the knee. At regions where the femoral component interfaces with the insert during extension and during an initial range of flexion of the knee, the femoral component's radius of curvature (R1) for flexion rotation is larger than its radius of curvature (R3) for varus/valgus rotation. In a preferred embodiment, the surface of the tibial tray is convex and spherically curved, and the insert is free to move in both the posterior-anterior direction and the medial-lateral direction with respect to the tibial tray.

60 Claims, 4 Drawing Sheets

SECTION EXT-EXT

FIG. 3D

SECTION FLEX-FLEX

SELF-ALIGNING KNEE PROSTHESIS

BACKGROUND OF THE INVENTION

The field of the invention relates to prosthetic devices for repairing joints such as the knee.

A wide variety of prosthetic devices for repairing knees are available. Some of these prosthetic devices are bicondylar, where both condyles of the knee are replaced. In situations where only one condyle of the knee is damaged, a unicondylar prosthetic device may be used. Unfortunately, early unicondylar designs were prone to failure unless they were installed with very precise alignment, which is difficult to achieve.

The Oxford unicondylar knee replacement is one prior art approach that attempts to solve this problem. In the Oxford knee, the insert is decoupled from the tray, so it can move with respect to both the tibial tray and the femoral component. Unfortunately, the decoupled insert has a high incidence of dislocation.

The inventors have recognized a need for an improved prosthetic device for repairing knees.

DETAILED DESCRIPTION OF THE PREFERRED EMBODIMENTS

FIGS. 1A–1D depict various views of a first embodiment of a unicondylar knee prosthesis, and the numbering of the various components in each of these figures is consistent. The knee prosthesis includes three main parts: a femoral component 10, a tibial tray 30, and an insert 20.

The femoral component 10 has a curved smooth outer surface 16, which enables it to form a sliding interface with the insert 20. The femoral component 10 also has a fixation surface to attach the femoral component 10 to the femur (not shown). In the illustrated embodiment, a peg 12 is provided for attachment to the femur and a structural member 14 provides strength and rigidity. Portions of the femur are typically cut or drilled away prior to installation to facilitate a stronger bond between the femur and the femoral component 10. Examples of suitable methods for fixing joint replacements to bone include using cement (e.g., polymethyl methacrylate) as a grout to attach the device to the bone, or adding a porous metal surface to the device and having bone grow into it and fix the device.

Figure 4A:
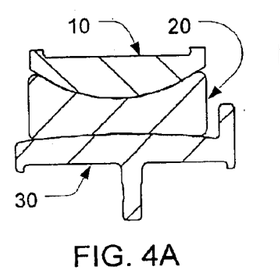
FIG. 4A is a front sectional view depicting the relationship between the three components of the second embodiment in neutral alignment.

The tibial tray 30 has a smooth upper sliding surface 34, which enables it to form a sliding interface with the insert 20. It also includes a suitable fixation surface to attach the tibial tray 30 to the tibial (not shown). In the illustrated embodiment, a keel 36 is provided for attachment to the tibia. The keel may be positioned off-center, as illustrated, or closer to the center of the tibial tray 30 in alternative embodiments (e.g., as shown in FIG. 4A). Appropriate drilling or cutting of the tibial may also be required in order to securely affix the tibial tray 30 on the tibia. The tibial tray 30 preferably also includes a raised ridge 32 located on the intercondylar side of the device to prevent dislocation of the insert 20 during use and to prevent abrasion of the insert by the adjacent bone.

Both the femoral component 10 and the tibial tray 30 are preferably made of a material that provides a smooth sliding surface, is sufficiently rigid and durable, and will not cause adverse patient reactions. Examples of suitable materials include cobalt chromium molybdenum alloy and appropriate ceramics.

The third main part of the prosthesis is the insert 20. The surface of the insert 20 that faces the femoral component 10 is called the femoral surface 26, and the surface of the insert 20 that faces the tibial component 30 is called the tibial surface 24. The insert 20 is preferably made of a material that can provide a good sliding interface with both the femoral component 10 and the tibial tray 30, and also provides good friction and wear characteristics. An example of a suitable material is ultra high molecular weight polyethylene.

When the device is inserted into a patient's knee, the insert 20 is sandwiched between the femoral component 10 and the tibial tray 30. The sliding surface 16 of the femoral component 10 forms a sliding interface with the femoral surface 26 of the insert 20, and the sliding surface 34 of the tibial tray 30 forms a sliding interface with the tibial surface 24 of the insert 20.

The shape of the femoral surface 26 of the insert 20 is matched to the sliding surface 16 of the femoral component 10 to provide a smooth sliding interface with a large contact area, so as to distribute the load over a relatively large area. In general, this will involve using approximately the same radius of curvature for both components. In cases where the sliding surface 16 of the femoral component 10 has a different shape in extension and flexion, the shape of the femoral surface 26 of the insert 20 is preferably matched to the shape of the sliding surface 16 of the femoral component 10 when the femoral component 10 is in extension.

Similarly, the shape of the tibial surface 24 of the insert 20 is matched to sliding surface 34 of the tibial tray 30 to provide a smooth sliding interface with a large contact area, to distribute the load over a relatively large area. In general, this will also involve using approximately the same radius of curvature for both components.

Figure 1A:
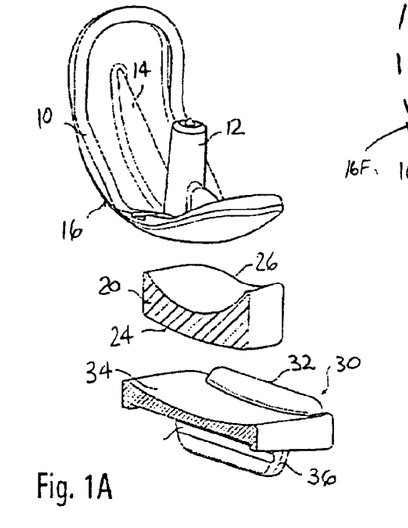
FIG. 1A is an exploded isometric view of a first embodiment of the invention with a front-to-back sectional view of the bottom two components.
Figure 1B:
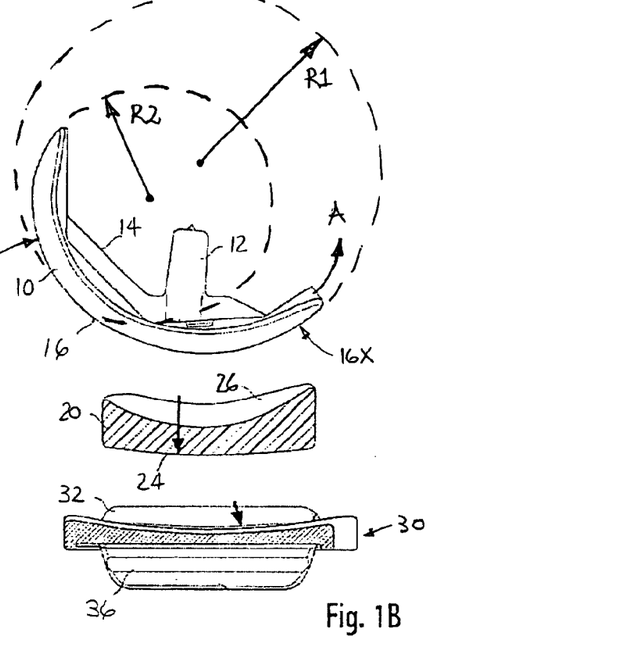
FIG. 1B is an exploded side view of the first embodiment with a front-to-back sectional view of the bottom two components.
Figures 1C, 1D:
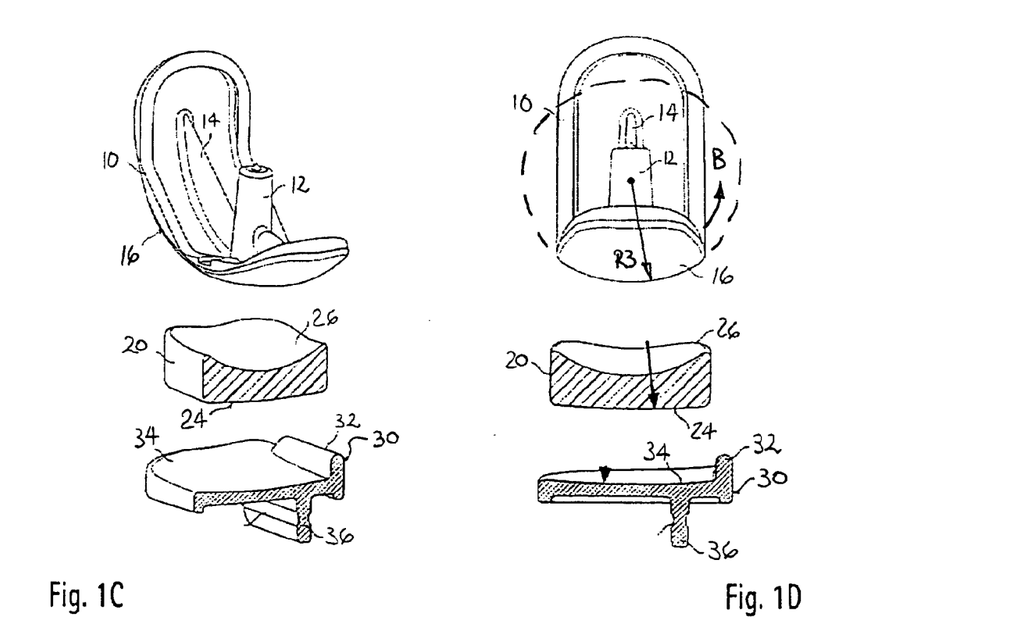
FIG. 1C is an exploded isometric view of the first embodiment with a side-to-side sectional view of the bottom two components.
FIG. 1D is an exploded front view of the first embodiment with a side-to-side sectional view of the bottom two components.
Figure 2A:
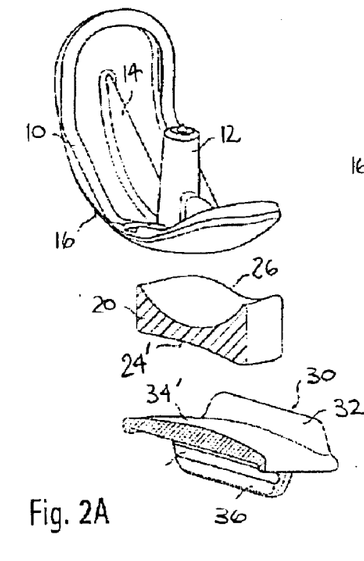
FIG. 2A is an exploded isometric view of a second embodiment of the invention with a front-to-back sectional view of the bottom two components.
Figure 2B:
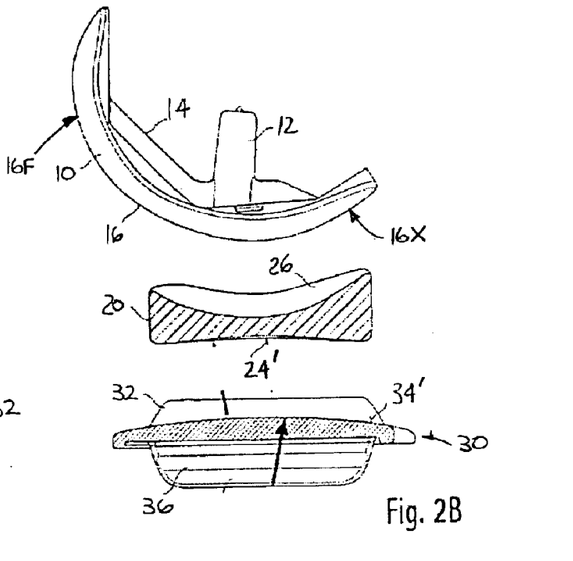
FIG. 2B is an exploded side view of the second embodiment with a front-to-back sectional view of the bottom two components.
Figure 2C:
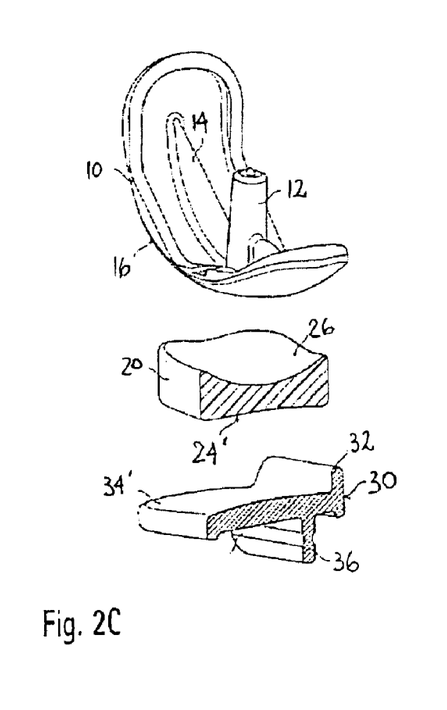
FIG. 2C is an exploded isometric view of the second embodiment with a side-to-side sectional view of the bottom two components.
Figure 2D:
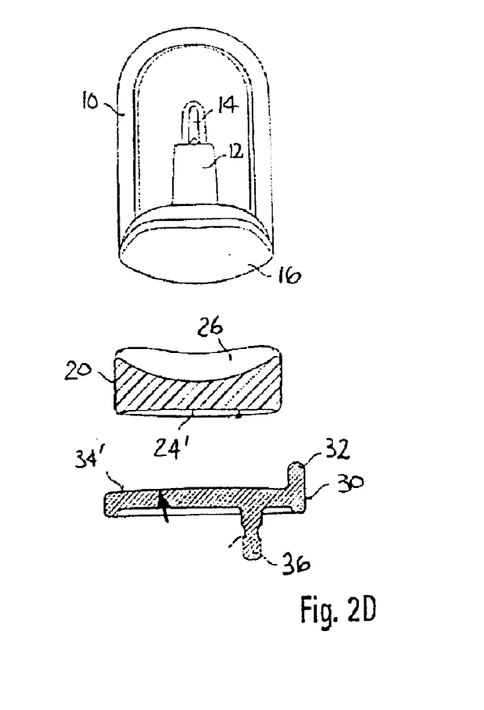
FIG. 2D is an exploded front view of the second embodiment with a side-to-side sectional view of the bottom two components.

A preferred shape for the sliding surface 16 of the femoral component 10 and femoral surface 26 of the insert 20 can best be seen in FIGS. 1B and 1D. In these figures, the components are arranged as they would appear when the knee is in extension. However, they are exploded apart in the figures to reveal the details of the device's construction.

As the knee is bent in flexion (i.e., rotation about a medial-lateral axis), the femoral component 10 will move with respect to the insert 20 and the tibial tray 30 by rotating counterclockwise (i.e., in the direction of the curved arrow labeled A in FIG. 1B.). In the illustrated embodiment, the sliding surface 16 of the femoral component 10 includes a first region 16$x$ with a first radius of curvature R1, and a second region 16$f$ with a second radius of curvature R2, where R2 is less than R1. Note that these radii of curvature R1 and R2 are the radii of rotation in flexion.

The region 16$f$ preferably extends far enough along the sliding surface 16 of the femoral component 10 so that during extension of the knee and during an initial range of flexion, the entire region of contact between the femoral component 10 and the insert 20 remains in region 16$x$. The femoral surface 26 of insert 20 is preferably matched to the radius R1.

During further flexion (i.e., flexion that exceeds the initial range of flexion), the femoral component 10 rotates further, and the second region 16$f$ moves into contact with the insert 20 as the first region 16$x$ moves away. Eventually, if the degree of flexion is increased beyond a certain point, the entire region of contact between the femoral component 10 and the insert 20 will occur in region 16$f$. The transition between the first region 16$x$ and the section region 16$f$ is preferably made at a point that is tangent to the circle defined by R1 as well as tangent to the circle defined by R2, to provide a smooth transition point. Using the two radii R1 and R2 in the femoral component 10 more closely mimics the morphology of the natural knee and reduces the amount of insert travel over the range of flexion of the knee.

In addition to pure flexion rotation, the knee may also experience varus/valgus rotation (i.e., rotation about an axis that is perpendicular to the coronal plane), which is indicated by the curved arrow labeled B in FIG. 1D. The radius of curvature for this varus/valgus rotation is labeled R3. Preferably, R1 is larger than R3. If R1 and R3 remain constant throughout the entire region 16$x$, the surface of the region 16$x$ would be toroidal.

Preferably, R2 is either greater than or equal to R3. If R2 and R3 remain constant throughout the entire region 16$f$, the surface of the region 16$f$ would also be a toroidal surface (or a spherical surface if R2=R3). In one preferred embodiment, for a medium sized device, R3 is about 19 mm, R1 is between about 30 mm and about 35 mm, and R2 is between about 20 mm and about 22 mm. These sizes may be scaled up or down appropriately for larger or smaller devices. In terms of ratios, R1 is preferably between about 1.5 and 1.9 times as large as R3, and R2 is preferably between about 1 and 1.2 times as large as R3.

While the illustrated embodiment shows that the sliding surface 16 of the femoral component 10 contains two regions 16$x$ and 16$f$ with different radii of curvature, an alternative embodiment may be implemented where the entire sliding surface 16 of the femoral component 10 has only a single radius of curvature R1 for flexion rotation, provided that that radius R1 is greater than the radius of curvature R3 for varus/valgus rotation. In another alternative embodiment, three or more regions with different radii of curvature may be used instead of the two illustrated regions 16$x$ and 16$f$. In still other alternative embodiments, the sliding surface 16 of the femoral component 10 may be splined to provide a gradual and continuous transition from a larger radius in extension to a smaller radius at full flexion. However, in each of these embodiments R1 is greater than R3, at least during extension and an initial range of flexion. This arrangement enables the insert 20 to follow the rotation of the femoral component 10 without spinning on the tibial tray 30. In contrast, the insert can spin on the tibial tray in the prior art Oxford design, so dislocation of the Oxford insert is more likely.

Turning now to the interface between the tibial tray 30 and the insert 20, a preferred shape for the sliding surface 34 of the tibial tray 30 and the tibial surface 24 of the insert 20 is a spherical surface. In this embodiment, the sliding surface 34 of the tibial tray 30 is spherically concave, and the tibial surface 24 of the insert 20 is spherically convex, with approximately the same radius of curvature as the sliding surface 34. In alternative embodiments (not shown), the sliding surface 34 of the tibial tray 30 is toroidally concave, and the tibial surface 24 of the insert 20 is toroidally convex, with approximately the same radii of curvature as the sliding surface 34. In another alternative embodiment (not shown), both the sliding surface 34 of the tibial tray 30 and the tibial surface 24 of the insert 20 are flat.

As the knee undergoes flexion rotation and varus/valgus rotation, as described above, the insert 20 is free to slide on the tibial tray 30 in all directions parallel to the tray surface, including the medial-lateral direction and the posterior-anterior direction, and will follow the femoral component 10. Of course, this freedom of motion only exists up to a certain point (e.g., when the insert 20 hits a portion of the patient's anatomy or the ridge 32 on the tibial tray 30). With this arrangement, the mating surfaces between the femoral component 10 and the insert 20, and between the tibial tray 30 and the insert 20, maintain alignment throughout the normal range of the motion of the knee. This keeps the region of contact between each of those parts relatively large, which distributes the load and reduces edge loading, both advantageous for preventing loosening of the components from their bony bed.

FIGS. 2A–2D depict various views of a second embodiment of a unicondylar knee prosthesis. This embodiment is similar to the first embodiment, except that in the second embodiment the sliding surface 34' of the tibial tray 30 is spherically convex and the tibial surface 24' of the insert 20 is correspondingly spherically concave. The remaining features are the same as their correspondingly-numbered counterparts in the first embodiment described above in connection with FIGS. 1A–1D. Preferably, the radius of curvature for the sliding surface 34' of the tibial tray 30 and the tibial surface 24' of the insert 20 is between about 100 and 300 mm, and most preferably about 120 mm. In alternative embodiments (not shown), the sliding surface 34 of the tibial tray 30 is toroidally convex, and the tibial surface 24 of the insert 20 is correspondingly toroidally concave.

Figure 5:
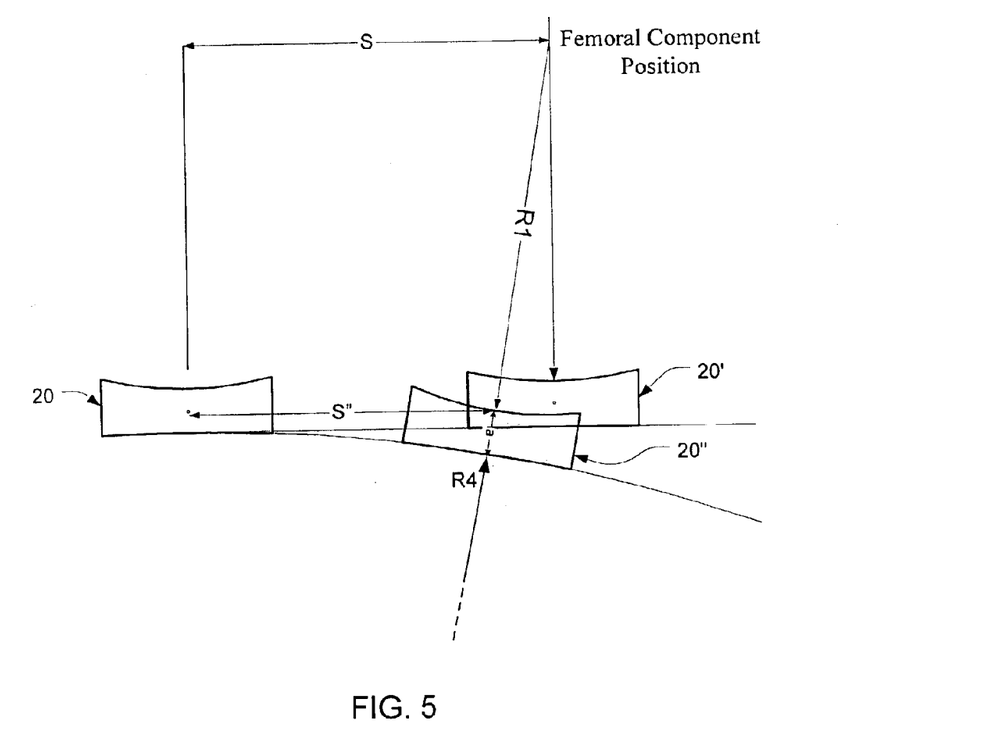
FIG. 5 is a schematic illustration of the translation reduction for the insert.

In both the first and second embodiments, the insert 20 follows the femoral component 10 when the femoral component 10 translates during normal flexion of the knee, and operation of the second embodiment is similar to the first embodiment. However, for a given amount of femoral translation, the corresponding translational movement of the insert 20 will be less for an insert that is sitting on a convex surface (as in the second embodiment) than it would be for an insert that is sitting on a flat or concave surface (as in the first embodiment). This reduction in insert translation is due to the orientation of the normal surface 34' of the tibial tray 30: an insert aligned to a convex surface will always be positioned more towards the center of the tibial tray 30 than an insert aligned to a flat or concave surface. For a hypothetical insert of thickness 'a' as shown in FIG. 5, where the femoral component undergoes a translation of S, the insert 20 will only experience a translation of S"=S×(R 4+a)/(R1+a+R 4). This amounts to a translation reduction of S×(R1/(R1+R4+a)), where R4 is the radius of curvature of the convex sliding surface 34' of the tibial tray 30 and R1 is the radius of curvature of the top surface of the insert.

A further advantage to using the bi-concave insert design is that it increases the amount of displacement needed to dislocate the insert 20, and is therefore less prone to dislocation. Additionally, the convex sliding surface 34' of the tibial tray 30 tends to direct the load applied by the femur towards the center of the tibial plateau, again minimizing edge loading and protecting against component loosening from the surrounding bone.

Figure 3A:
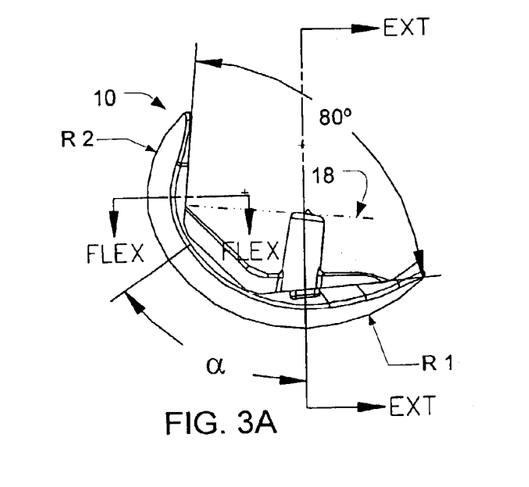
FIG. 3A is a detail of the side view of the femoral component for the first and second embodiments.

FIG. 3A is a side view of the femoral component 10 with dimensions that indicate the point where the first radius R1 ends and the second radius R2 begins. That point occurs at an angle α (assuming a base line of α=0° that lines up with the proximal-distal axis of the leg in extension). Preferably, α is between 25° and 80° and more preferably between 28° and 55°.

Figure 3B:
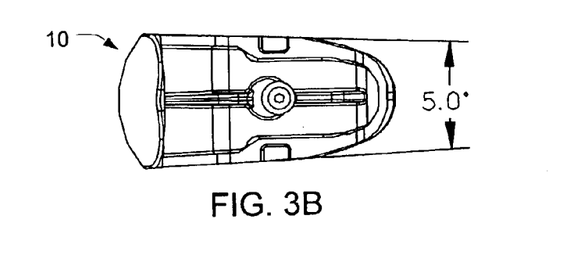
FIG. 3B is a detail of the top view of the femoral component shown in FIG. 3A.
Figure 3C:
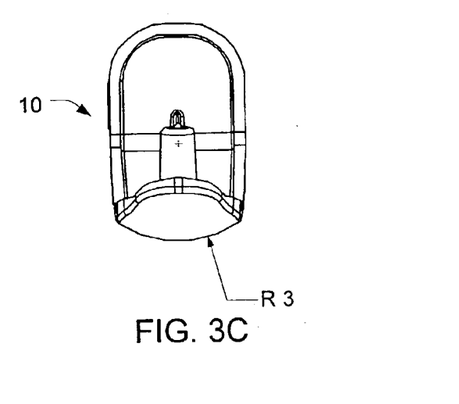
FIG. 3C is a detail of the front view of the femoral component shown in FIG. 3A.
Figure 3D:
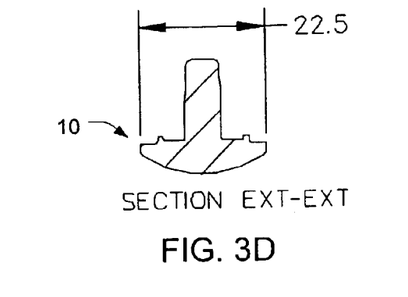
FIG. 3D is a first section view of the femoral component shown in FIG. 3A.
Figure 3E:
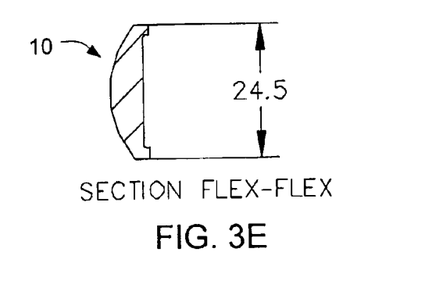
FIG. 3E is a second section view of the femoral component shown in FIG. 3A.
Figure 3F:
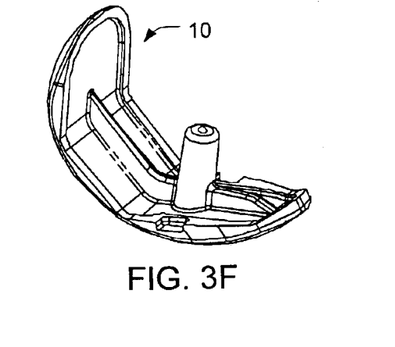
FIG. 3F is an isometric view of the femoral component shown in FIG. 3A.

FIG. 3B is a top view of the femoral component 10. This view illustrates an optional feature that can be used with the first and second embodiments described above. With this option, the anterior end of the femoral component is tapered at an angle that is preferably about 5° degrees. Tapering the femoral component 10 so that it is wider posteriorly than anteriorly advantageously provides more contact area and allows for more varus/valgus rotation when the knee is in flexion without taking up too much space when the knee is in extension.

In the first and second embodiments, the height of the structural member 14 is preferably approximately equal to the height of the peg 12 when measured parallel to the posterior bone cut (as shown by the construction line 18 in FIG. 3A). This configuration prevents the femoral component 10 from tilting when inserted. The angle between the posterior cut surface and the distal cut surface is preferably less than 90° (e.g., about 80°, as shown in FIG. 3A). This advantageously preserves bone stock and increases the flexion range of motion.

Figure 4B:
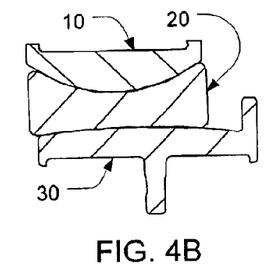
FIG. 4B is a detail view depicting the relationship between the three components of the second embodiment in translational misalignment.
Figure 4C:
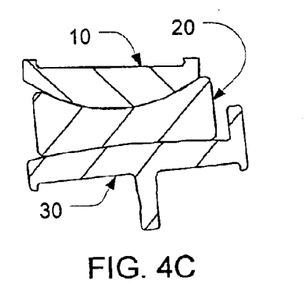
FIG. 4C is a detail view depicting the relationship between the three components of the second embodiment in a rotational misalignment.

The second embodiment advantageously provides a good load-bearing contact between the femoral component 10, the insert 20, and the tibial tray 30 without edge-loading the insert, even when the device is not perfectly aligned during installation. FIG. 4A shows the position of the various components as they would appear after a perfectly aligned installation. FIG. 4B shows how those components would align if the tibial tray 30 and the femoral component 10 are installed with an offset in the medial-lateral axis. In this case, the insert 20 would slide towards the left so as to maintain a good contact with both the femoral component 10 and the tibial tray 30. FIG. 4C shows how those components would align if the tibial tray 30 and the femoral component 10 are installed with a varus/valgus rotational offset. Here, the insert 20 would rotate so as to maintain a good contact with both the femoral component 10 and the tibial tray 30.

While all of the embodiments described herein are unicondylar, persons skilled in the relevant arts will recognize that a bicondylar knee prosthesis may also be implemented using similar principles. In addition, the principles described herein may be applied to other joints in human or animal bodies including, for example, the ankle and the spine (e.g., for intervertebral disc replacements). Finally, while the present invention has been described in the context of the above-described embodiments, various changes may be made to those embodiments and various equivalents may be substituted without departing from the scope of the invention, as will be apparent to persons skilled in the relevant arts.

We claim:

1. A knee joint prosthesis comprising:
   a femoral component having a fixation surface configured for attaching to a femur and a sliding surface;
   a tibial tray having a fixation surface configured for attaching to a tibial and a sliding surface; and
   an insert that fits between the femoral component and the tibial tray when the prosthesis is installed in a subject, the insert having a femoral side and a tibial side, wherein the femoral side is shaped to slidingly interface with the sliding surface of the femoral component during flexion of the knee and the tibial side is shaped to slidingly interface with the sliding surface of the tibial tray,
   wherein, at regions where the sliding surface of the femoral component interfaces with the insert during extension and an initial range of flexion of the knee, a radius of curvature (R1) of the sliding surface of the femoral component for flexion rotation is larger than a radius of curvature (R3) of the sliding surface of the femoral component for varus/valgus rotation, and
   wherein the sliding surface of the tibial tray is spherically or toroidally curved.

2. The prosthesis of claim 1, wherein the sliding surface of the tibial tray is convex and the tibial side of the insert is concave.

3. The prosthesis of claim 1, wherein R1 is between about 1.5 and 1.9 times as large as R3.

4. The prosthesis of claim 1, wherein, at regions where the sliding surface of the femoral component interfaces with the insert when flexion of the knee exceeds the initial range, a radius of curvature (R2) of the sliding surface of the femoral component for flexion rotation is less than R1.

5. The prosthesis of claim 1, wherein, at regions where the sliding surface of the femoral component interfaces with the insert when flexion of the knee exceeds the initial range, a radius of curvature (R2) of the sliding surface of the femoral component for flexion rotation is larger than or equal to R3, and wherein R2 is less than R1.

6. The prosthesis of claim 5, wherein R1 is between about 1.5 and 1.9 times as large as R3, R2 is between about 1 and 1.2 times as large as R3, and the transition between R1 and R2 occurs at between about 280° and about 55° with respect to a proximal-distal axis.

7. The prosthesis of claim 6, wherein the sliding surface of the tibial tray is convex and the tibial side of the insert is concave.

8. A knee joint prosthesis comprising:
a femoral component having a fixation surface configured for attaching to a femur and a sliding surface;
a tibial tray having a fixation surface configured for attaching to a tibial and a sliding surface; and
an insert that fits between the femoral component and the tibial tray when the prosthesis is installed in a subject, the insert having a femoral side and a tibial side, wherein the femoral side is shaped to slidingly interface with the sliding surface of the femoral component during flexion of the knee and the tibial side is shaped to slidingly interface with the sliding surface of the tibial tray,
wherein, at regions where the sliding surface of the femoral component interfaces with the insert during extension and an initial range of flexion of the knee, a radius of curvature (R1) of the sliding surface of the femoral component for flexion rotation is larger than a radius of curvature (R3) of the sliding surface of the femoral component for varus/valgus rotation, and
wherein the insert is free to move in both the posterior-anterior direction and the medial-lateral direction with respect to the tibial tray.

9. The prosthesis of claim 8, wherein R1 is between about 1.5 and 1.9 times as large as R3.

10. The prosthesis of claim 8, wherein, at regions where the sliding surface of the femoral component interfaces with the insert when flexion of the knee exceeds the initial range, a radius of curvature (R2) of the sliding surface of the femoral component for flexion rotation is less than R1.

11. The prosthesis of claim 8, wherein, at regions where the sliding surface of the femoral component interfaces with the insert when flexion of the knee exceeds the initial range, a radius of curvature (R2) of the sliding surface of the femoral component for flexion rotation is larger than or equal to R3, end wherein R2 is less than R1.

12. The prosthesis of claim 11, wherein R1 is between about 1.5 and 1.9 times as large as R3, R2 is between about 1 and 1.2 times as large as R3, and the transition between R1 and R2 occurs at between about 28° and about 55° with respect to a proximal-distal axis.

13. A knee joint prosthesis comprising:
a femoral component having a fixation surface configured for attaching to a femur and a sliding surface;
a tibial tray having a fixation surface configured for attaching to a tibial and a sliding surface; and
an insert that fits between the femoral component and the tibial tray when the prosthesis is installed in a subject, the insert having a femoral side and a tibial side, wherein the femoral side is shaped to slidingly interface with the sliding surface of the femoral component during flexion of the knee and the tibial side is shaped to slidingly interface with the sliding surface of the tibial tray,
wherein, at regions where the sliding surface of the femoral component interfaces with the insert during extension and an initial range of flexion of the knee, a radius of curvature (R1) of the sliding surface of the femoral component for flexion rotation is larger than a radius of curvature (R3) of the sliding surface of the femoral component for varus/valgus rotation, wherein the sliding surface of the tibial tray is spherically curved and convex, and the tibial side of the insert is concave, and
wherein the insert is free to move in both the posterior-anterior direction and the medial-lateral direction with respect to the tibial tray.

14. The prosthesis of claim 13, wherein R1 is between about 1.5 and 1.9 times as large as R3.

15. The prosthesis of claim 13, wherein, at regions where the sliding surface of the femoral component interfaces with the insert when flexion of the knee exceeds the initial range, a radius of curvature (R2) of the sliding surface of the femoral component for flexion rotation is less than R1.

16. The prosthesis of claim 13, wherein, at regions where the sliding surface of the femoral component interfaces with the insert when flexion of the knee exceeds the initial range, a radius of curvature (R2) of the sliding surface of the femoral component for flexion rotation is larger than or equal to R3, and wherein R2 is less than R1.

17. The prosthesis of claim 16, wherein R1 is between about 1.5 and 1.9 times as large as R3, R2 is between about 1 and 1.2 times as large as R3, and the transition between R1 and R2 occurs at between about 28° and about 55° with respect to a proximal-distal axis.

18. A joint prosthesis comprising:
a first component having a fixation surface configured for attaching to a first bone and a sliding surface;
a second component having a fixation surface configured for attaching to a second bone and a sliding surface; and
an insert that fits between the first component and the second component when the prosthesis is installed in a subject, the insert having a first side and a second side, wherein the first side is shaped to slidingly interface with the sliding surface of the first component during flexion of the joint and the second side is shaped to slidingly interface with the sliding surface of the second component,
wherein, at regions where the sliding surface of the first component interfaces with the insert during extension and an initial range of flexion of the joint, a radius of curvature (R1) of the sliding surface of the first component for flexion rotation is larger than a radius of curvature (R3) of the sliding surface of the first component for rotation about an axis that is perpendicular to the coronal plane of the subject, and
wherein the sliding surface of the second component is spherically or toroidally curved.

19. A joint prosthesis comprising:
a first component having a fixation surface configured for attaching to a first bone and a sliding surface;
a second component having a fixation surface configured for attaching to a second bone and a sliding surface; and
an insert that fits between the first component and the second component when the prosthesis is installed in a subject, the insert having a first side and a second side, wherein the first side is shaped to slidingly interface with the sliding surface of the first component during flexion of the joint and the second side is shaped to slidingly interface with the sliding surface of the second component,
wherein, at regions where the sliding surface of the first component interfaces with the insert during extension and an initial range of flexion of the joint, a radius of curvature (R1) of the sliding surface of the first component for flexion rotation is larger than a radius of curvature (R3) of the sliding surface of the first component for rotation about an axis that is perpendicular to the coronal plane of the subject, and wherein the insert is free to move in both the posterior-anterior direction and the medial-lateral direction with respect to the second component.

20. The prosthesis of claim 1, wherein the femoral component is tapered so that it is wider posteriorly than anteriorly.

21. The prosthesis of claim 1, wherein the femoral component is tapered so that it is wider posteriorly than anteriorly by about 5°.

22. The prosthesis of claim 1, wherein an angle between the posterior cut surface and the distal cut surface of the femoral component is less than 90°.

23. The prosthesis of claim 1, wherein an angle between the posterior cut surface and the distal cut surface of the femoral component is about 80°.

24. The prosthesis of claim 8, wherein the femoral component is tapered so that it is wider posteriorly than anteriorly.

25. The prosthesis of claim 8, wherein the femoral component is tapered so that it is wider posteriorly than anteriorly by about 5°.

26. The prosthesis of claim 8, wherein an angle between the posterior cut surface and the distal cut surface of the femoral component is less than 90°.

27. The prosthesis of claim 8, wherein an angle between the posterior cut surface and the distal cut surface of the femoral component is about 80°.

28. The prosthesis of claim 13, wherein the femoral component is tapered so that it is wider posteriorly than anteriorly.

29. The prosthesis of claim 13, wherein the femoral component is tapered so that it is wider posteriorly than anteriorly by about 5°.

30. The prosthesis of claim 13, wherein an angle between the posterior cut surface and the distal cut surface of the femoral component is less than 90°.

31. The prosthesis of claim 13, wherein an angle between the posterior cut surface and the distal cut surface of the femoral component is about 80°.

32. A knee joint prosthesis comprising:
a unicondylar femoral component having a fixation surface configured for attaching to a femur and a sliding surface;
a unicondylar tibial tray having a fixation surface configured for attaching to a tibial and a sliding surface; and
a unicondylar insert that fits between the femoral component and the tibial tray when the prosthesis is installed in a subject, the insert having a femoral side and a tibial side, wherein the femoral side is shaped to slidingly interface with the sliding surface of the femoral component during flexion of the knee and the tibial side is shaped to slidingly interface with the sliding surface of the tibial tray,
wherein, at regions where the sliding surface of the femoral component interfaces with the insert during extension and an initial range of flexion of the knee, a radius of curvature (R1) of the sliding surface of the femoral component for flexion rotation is larger than a radius of curvature (R3) of the sliding surface of the femoral component for varus/valgus rotation, and
wherein the sliding surface of the tibial tray is spherically or toroidally curved.

33. The prosthesis of claim 32, wherein the sliding surface of the tibial tray is convex and the tibial side of the insert is concave.

34. The prosthesis of claim 32, wherein R1 is between about 1.5 and 1.9 times as large as R3.

35. The prosthesis of claim 32, wherein, at regions where the sliding surface of the femoral component interfaces with the insert when flexion of the knee exceeds the initial range, a radius of curvature (R2) of the sliding surface of the femoral component far flexion rotation is less than R1.

36. The prosthesis of claim 32, wherein, at regions where the sliding surface of the femoral component interfaces with the insert when flexion of the knee exceeds the initial range, a radius of curvature (R2) of the sliding surface of the femoral component for flexion rotation is larger than or equal to R3, and wherein R2 is less than R1.

37. The prosthesis of claim 36, wherein R1 is between about 1.5 and 1.9 times as large as R3, R2 is between about 1 and 1.2 times as large as R3, and the transition between R1 and R2 occurs at between about 28° and about 55° with respect to a proximal-distal axis.

38. The prosthesis of claim 37, wherein the sliding surface of the tibial tray is convex and the tibial side of the insert is concave.

39. The prosthesis of claim 32, wherein the femoral component is tapered so that it is wider posteriorly than anteriorly.

40. The prosthesis of claim 32, wherein the femoral component is tapered so that it is wider posteriorly than anteriorly by about 5°.

41. The prosthesis of claim 32, wherein an angle between the posterior cut surface and the distal cut surface of the femoral component is less than 90°.

42. The prosthesis of claim 32, wherein an angle between the posterior cut surface and the distal cut surface of the femoral component is about 80°.

43. A knee joint prosthesis comprising:
a unicondylar femoral component having a fixation surface configured for attaching to a femur and a sliding surface;
a unicondylar tibial tray having a fixation surface configured for attaching to a tibial and a sliding surface; and
a unicondylar insert that fits between the femoral component and the tibial way when the prosthesis is installed in a subject, the insert having a femoral side and a tibial side, wherein the femoral side is shaped to slidingly interface with the sliding surface of the femoral component during flexion of the knee and the tibial side is shaped to slidingly interface with the sliding surface of the tibial tray,
wherein, at regions where the sliding surface of the femoral component interfaces with the insert during extension and an initial range of flexion of the knee, a radius of curvature (R1) of the sliding surface of the femoral component for flexion rotation is larger than a radius of curvature (R3) of the sliding surface of the femoral component for varus/valgus rotation, and
wherein the insert is free to move in both the posterior-anterior direction and the medial-lateral direction with respect to the tibial tray.

44. The prosthesis of claim 43, wherein R1 is between about 1.5 and 1.9 times as large as R3.

45. The prosthesis of claim 43, wherein, at regions where the sliding surface of the femoral component interfaces with the insert when flexion of the knee exceeds the initial range, a radius of curvature (R2) of the sliding surface of the femoral component for flexion rotation is less than R1.

46. The prosthesis of claim 43, wherein, at regions where the sliding surface of the femoral component interfaces with the insert when flexion of the knee exceeds the initial range, a radius of curvature (R2) of the sliding surface of the femoral component for flexion rotation is larger than or equal to R3, and wherein R2 is less than R1.

47. The prosthesis of claim 46, wherein R1 is between about 1.5 and 1.9 times as large as R3, R2 is between about 1 and 1.2 times as large as R3, and the transition between R1 and R2 occurs at between about 28° and about 55° with respect to a proximal-distal axis.

48. The prosthesis of claim 43, wherein the femoral component is tapered so that it is wider posteriorly than anteriorly.

49. The prosthesis of claim 43, wherein the femoral component is tapered so that it is wider posteriorly than anteriorly by about 5°.

50. The prosthesis of claim 43, wherein an angle between the posterior cut surface and the distal cut surface of the femoral component is less than 90°.

51. The prosthesis of claim 43, wherein an angle between the posterior cut surface and the distal cut surface of the femoral component is about 80°.

52. A knee joint prosthesis comprising:
a unicondylar femoral component having a fixation surface configured for attaching to a femur and a sliding surface;
a unicondylar tibial tray having a fixation surface configured for attaching to a tibial and a sliding surface; and
a unicondylar insert that fits between the femoral component and the tibial tray when the prosthesis is installed in a subject, the insert having a femoral side and a tibial side, wherein the femoral side is shaped to slidingly interface with the sliding surface of the femoral component during flexion of the knee and the tibial side is shaped to slidingly interface with the sliding surface of the tibial tray,
wherein, at regions where the sliding surface of the femoral component interfaces with the insert during extension and an initial range of flexion of the knee, a radius of curvature (R1) of the sliding surface of the femoral component for flexion rotation is larger than a radius of curvature (R3) of the sliding surface of the femoral component for varus/valgus rotation,
wherein the sliding surface of the tibial tray is spherically curved and convex, and the tibial side of the insert is concave, and
wherein the insert is free to move in both the posterior-anterior direction and the medial-lateral direction with respect to the tibial tray.

53. The prosthesis of claim 52, wherein R1 is between about 1.5 and 1.9 times as large as R3.

54. The prosthesis of claim 52, wherein, at regions where the sliding surface of the femoral component interfaces with the insert when flexion of the knee exceeds the initial range, a radius of curvature (R2) of the sliding surface of the femoral component for flexion rotation is less than R1.

55. The prosthesis of claim 52, wherein, at regions where the sliding surface of the femoral component interfaces with the insert when flexion of the knee exceeds the initial range, a radius of curvature (R2) of the sliding surface of the femoral component for flexion rotation is larger than or equal to R3, and wherein R2 is less than R1.

56. The prosthesis of claim 55, wherein R1 is between about 1.5 and 1.9 times as large as R3, R2 is between about 1 and 1.2 times as large R3, and the transition between R1 and R2 occurs at between about 28° and about 55° with respect to a proximal-distal axis.

57. The prosthesis of claim 52, wherein the femoral component is tapered so that it is wider posteriorly than anteriorly.

58. The prosthesis of claim 52, wherein the femoral component is tapered so that it is wider posteriorly than anteriorly by about 5°.

59. The prosthesis of claim 52, wherein an angle between the posterior cut surface and the distal cut surface of the femoral component is less than 90°.

60. The prosthesis of claim 52, wherein an angle between the posterior cut surface and the distal cut surface of the femoral component is about 80°.

* * * * *

UNITED STATES PATENT AND TRADEMARK OFFICE
CERTIFICATE OF CORRECTION

PATENT NO. : 7,105,027 B2 Page 1 of 1
APPLICATION NO. : 10/356657
DATED : September 12, 2006
INVENTOR(S) : Joseph D. Lipman et al.

It is certified that error appears in the above-identified patent and that said Letters Patent is hereby corrected as shown below:

Column 6
Line 31, change "to a tibial" to --to a tibia--.

Column 7
Line 2, change "280°"" to --28°--.
Line 11, change "to a tibial" to --to a tibia--.
Line 42, change "end" to --and--.
Line 52, change "to a tibial" to --to a tibia--.

Column 9
Line 47, change "to a tibial" to --to a tibia--.

Column 10
Line 7, change "far" to --for--.
Line 40, change "to a tibial" to --to a tibia--.
Line 42, change "way" to --tray--.

Column 11
Line 28, change "to a tibial" to --to a tibia--.

Column 12
Line 25, change "large R3" to --large as R3--.

Signed and Sealed this

Ninth Day of January, 2007

JON W. DUDAS
*Director of the United States Patent and Trademark Office*